US008663681B2

(12) United States Patent
Ahmed et al.

(10) Patent No.: US 8,663,681 B2
(45) Date of Patent: Mar. 4, 2014

(54) ORAL DOSAGE FORMS COMPRISING PROGESTERONE AND METHODS OF MAKING AND USING THE SAME

(75) Inventors: Salah U. Ahmed, New City, NY (US); Charles E. Diliberti, Montclair, NJ (US); Chandra Vattikonda, Towaco, NJ (US); Sudhir R. Gorukanti, Harriman, NY (US); Sanjeev K. Gupta, Washington Township, NJ (US)

(73) Assignee: Teva Women's Health, Inc., Woodcliff Lake, NJ (US)

( * ) Notice: Subject to any disclaimer, the term of this patent is extended or adjusted under 35 U.S.C. 154(b) by 1911 days.

(21) Appl. No.: 11/441,447

(22) Filed: May 26, 2006

(65) Prior Publication Data

US 2006/0275360 A1     Dec. 7, 2006

Related U.S. Application Data

(60) Provisional application No. 60/684,557, filed on May 26, 2005.

(51) Int. Cl.
*A61K 31/56* (2006.01)

(52) U.S. Cl.
USPC ............ 424/451; 424/408; 424/452; 514/9.8; 514/10.1; 514/177

(58) Field of Classification Search
USPC ........... 514/9.8, 10.1, 177; 424/408, 452, 451
See application file for complete search history.

(56) References Cited

U.S. PATENT DOCUMENTS

| | | | |
|---|---|---|---|
| 4,196,188 A | 4/1980 | Besins | |
| 4,439,432 A | 3/1984 | Peat | |
| 4,900,734 A | 2/1990 | Maxson et al. | |
| 4,927,816 A | 5/1990 | Ester | |
| 4,963,540 A * | 10/1990 | Maxson et al. | ............... 514/177 |
| 5,140,021 A | 8/1992 | Maxson et al. | |
| 5,514,673 A | 5/1996 | Heckenmüller et al. | |
| 5,620,705 A | 4/1997 | Dong et al. | |
| 5,633,011 A | 5/1997 | Dong et al. | |
| 5,645,856 A | 7/1997 | Lacy et al. | |
| 5,770,227 A | 6/1998 | Dong et al. | |
| 5,908,638 A | 6/1999 | Huber et al. | |
| 6,001,336 A | 12/1999 | Gordon | |
| 6,030,988 A | 2/2000 | Gilis et al. | |
| 6,086,916 A | 7/2000 | Agnus et al. | |
| 6,096,338 A | 8/2000 | Lacy et al. | |
| 6,248,363 B1 | 6/2001 | Patel et al. | |
| 6,267,985 B1 | 7/2001 | Chen et al. | |
| 6,294,192 B1 | 9/2001 | Patel et al. | |
| 6,787,531 B1 | 9/2004 | Hilman et al. | |
| 2003/0004145 A1 | 1/2003 | Leonard | |
| 2003/0092691 A1 | 5/2003 | Besse et al. | |
| 2003/0143276 A1* | 7/2003 | Hsia et al. | ..................... 424/486 |
| 2003/0191096 A1 | 10/2003 | Leonard et al. | |
| 2004/0052824 A1* | 3/2004 | Abou Chacra-Vernet et al. | ................... 424/400 |
| 2004/0072808 A1 | 4/2004 | Leonard | |
| 2004/0131553 A1 | 7/2004 | Besse | |
| 2004/0259851 A1 | 12/2004 | Leonard | |
| 2005/0008704 A1 | 1/2005 | Ray et al. | |
| 2006/0182691 A1 | 8/2006 | Besse et al. | |

FOREIGN PATENT DOCUMENTS

| | | | |
|---|---|---|---|
| EA | 000804 B1 | 4/2000 | |
| FR | 2 851 918 A1 | 9/2004 | |
| WO | WO 91/18613 A1 | 12/1991 | |
| WO | WO0130355 | * 5/2001 | ........... A61K 31/565 |

OTHER PUBLICATIONS

Майоров, М.В., Foreign language article available at: <http://www.provisor.com.ua/archive/2004/N7/art_26.htm?part_code=8& art_code=4106> as accessed on May 28, 2008.
Филатова, Е.В., Russian language article available at: <http://hghltd.yandex.net/yandbtm?url=http%3A%2F%2Fwww.goodreferats.ru%2Fwat ... > as accessed on May 28, 2008.
Иванов, Е.Г., Foreign language article available at: <www.helmi.ru/aw/articles/a7.htm> as accessed Sep. 10, 2008.
Утрожестан, Foreign language article available at: <http://hghltd.yandex.net/yandbtm?url=http%3A%2F%2Fwww.umj.com.ua%2 Farhiv ... > as accessed May 28, 2008.
Утрожестан, Foreign language article available at: <http://hghltd.yandex.net/yandbtm?url=http%3A%2F%2Fwww.piluli.com.ua%2Fnotes ... > as accessed May 28, 2008.
Eurasian search report for Eurasian Patent Application No. 200702627, filed May 26, 2006, dated May 16, 2008 (in Russian).
An Official Action for Eurasian Patent Application No. 200702627, filed May 26, 2006, dated Oct. 2, 2009 (in Russian).
Wade, A., et al., *Handbook of Pharmaceutical Excipients*, $3^{rd}$ edition., pp. 651, Kibbe, A. H., ed., American Pharmaceutical Association, United States (2000).
Solvay Pharmaceuticals, Inc., "Prometrium," information sheet for compliance with FDA regulations (2009); 19 pages.
Wikipedia, "Excipient," retrieved from the internet on Sep. 7, 2010 at http://en.wikipedia.org/w/index.php?title=Excipient& printable=yes, 4 pages.
Mentions légales: "Utrogestan", retrieved from the internet on Sep. 7, 2010 at http://pro.gyneweb.fr/sources/industrie/labo/besins/utrogestan.html, 3 pages.
English-translation (unverified-machine generated) of Mentions légales: "Utrogestan", retrieved from the internet on Jan. 31, 2011 at http://translate.google.com/translate?js=n&prev=_t&hl=en&ie—UTF-8&layout=2&eotf=1&s1=fr&t1=en& u=http%3A%2F%2Fpro.gyneweb.fr%2Fsources%2 Findustrie%2Flabo%2Fbesins%2Futrogestan.html&act=url, 2 pages.

(Continued)

*Primary Examiner* — Rebecca Prouty
*Assistant Examiner* — Danielle Sullivan
(74) *Attorney, Agent, or Firm* — Sterne, Kessler, Goldstein & Fox P.L.L.C.

(57) ABSTRACT

The present invention relates to an oral pharmaceutical dosage form comprising micronized progesterone, an edible oil, a disintegrant, and a hydrophilic excipient. Particularly, the invention relates to a pharmaceutical dosage form wherein the dosage form is in a powder form and is contained in a pharmaceutically acceptable capsule. The present invention is also directed toward methods of making the dosage form, methods of using the dosage form, and kits comprising the dosage form.

21 Claims, 1 Drawing Sheet

(56) References Cited

OTHER PUBLICATIONS

European Search Report for EP Application No. 06 771 398.2, European Patent Office, Netherlands, dated Sep. 27, 2010; 9 pages.
International Search Report of International Application No. PCT/US2006/020609, European Patent Office, Netherlands, mailed on Feb. 23, 2007.
Farinha, A., et al., "Improved Bioavailability of a Micronized Megestrol Acetate Tablet Formulation in Humans," *Drug Dev. Industr. Pharm.* 26:567-570, Marcel Dekker, Inc. (2000).
Gusberg, S.B. and Hall, R.E., "Precursors of Corpus Cancer. III. The Appearance of Cancer of the Endometrium in Estrogenically Conditioned Patients," *Obstretr. Gynecol. 17*:397-412, (1961).
Moghissi, K.S. and Winkel, C.A., "Medical Management of Endometriosis," *ACOG Practice Bulletin No. 11, Clinical Management Guidelines for Obstetrician-Gynecologists*, pp. 1-14, The American College of Obstetricians and Gynecologists (1999).
Soules, M.R., et al., "Luteal Phase Deficiency: Characterization of Reproductive Hormones over the Menstrual Cycle," *J. Clin. Endocrinol. Metab.* 69:804-812, Endocrine Society (1989).

\* cited by examiner

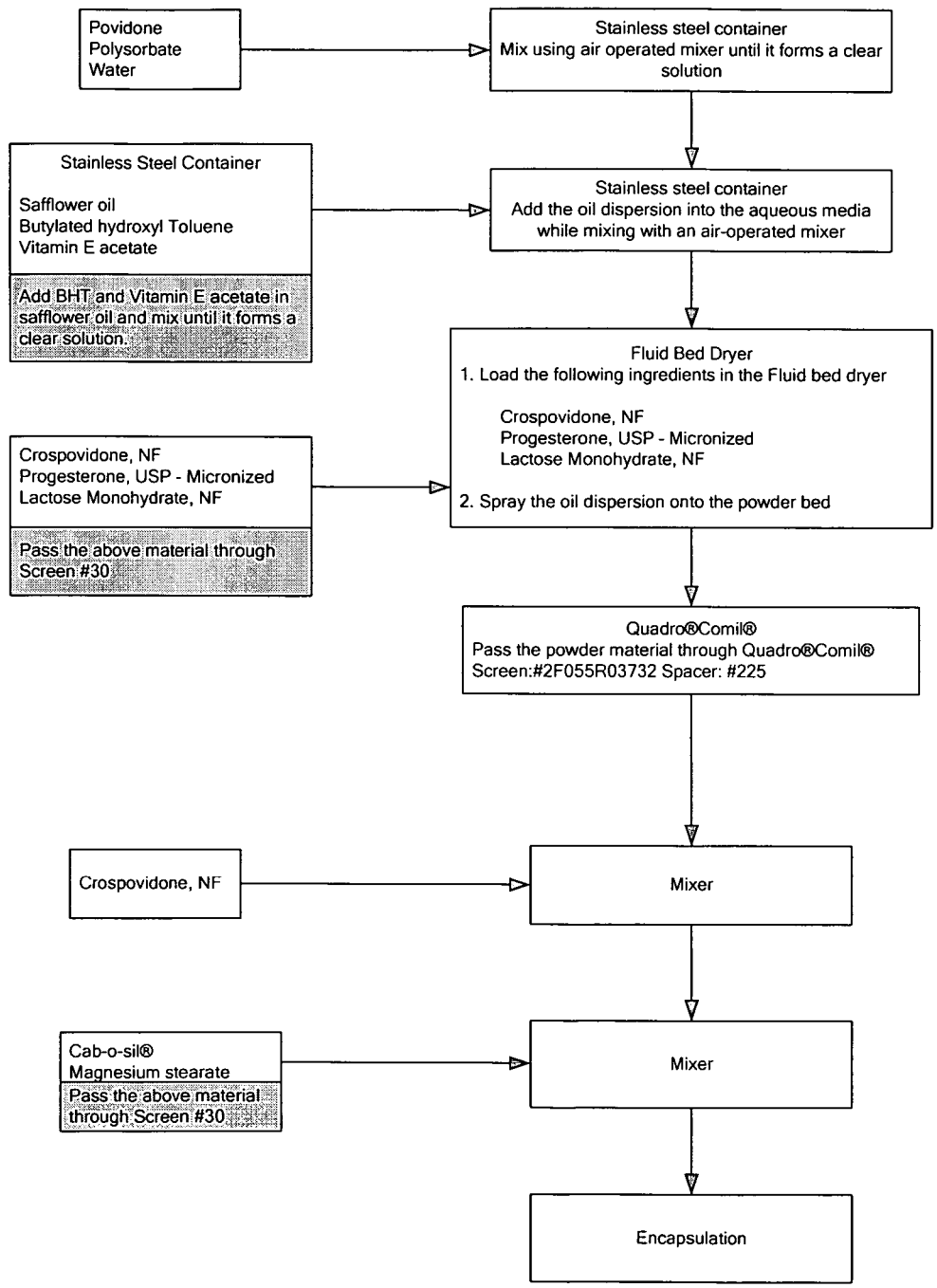

ORAL DOSAGE FORMS COMPRISING PROGESTERONE AND METHODS OF MAKING AND USING THE SAME

CROSS-REFERENCE TO RELATED APPLICATION

This application claims the benefit of the filing date of U.S. application Ser. No. 60/684,557, filed May 26, 2005, which is hereby incorporated by reference in its entirety.

BACKGROUND OF THE INVENTION

1. Field of the Invention

The present invention relates to an oral pharmaceutical dosage form comprising micronized progesterone, an edible oil, a disintegrant, and a hydrophilic excipient.

Particularly, the invention relates to a pharmaceutical dosage form wherein the dosage form is in a powder form and is contained in a pharmaceutically acceptable capsule.

2. Background Art

In the United States, Prometrium® is currently the primary orally administered dosage form of progesterone. Prometrium® capsules are available in either 100 mg or 200 mg capsules. These soft gelatin capsules contain a suspension of progesterone in a fluid consisting primarily of peanut oil. Prometrium® capsules are indicated for use in the prevention of endometrial hyperplasia in non-hysterectomized postmenopausal women who are receiving conjugated estrogen tablets and for use in treating secondary amenorrhea. However, Prometrium® capsules can have an erratic absorption profile, can have content leakage from the capsule, and are not suitable for patients who are allergic to peanut oil.

Others have tried to produce dosage forms containing progesterone to overcome some of the deficiencies in current products. Tablets, capsules, inhalation powders, oil suspensions, and other dosage forms containing progesterone are disclosed in U.S. Pat. Nos. 4,900,734, 4,963,540, 5,620,705, and 6,001,336. However, these dosage forms do not have the advantages of the present invention.

BRIEF SUMMARY OF THE INVENTION

The present invention is directed to an oral pharmaceutical dosage form, methods of making the dosage form, methods of using the dosage form, methods of educating persons about the dosage form, and kits comprising the dosage form.

The present invention is directed to oral pharmaceutical dosage forms comprising progesterone. Some embodiments of the present invention include an oral pharmaceutical dosage form comprising: micronized progesterone, an edible oil, a disintegrant, and a hydrophilic excipient; wherein the dosage form is in a powder form and is contained in a pharmaceutically acceptable capsule. In some embodiments, the disintegrant is crospovidone.

In some embodiments, the dosage forms of the present invention can further comprise one or more of the following: an absorbant, an antioxidant, a lubricant, or any other excipient known to one of skill in the art.

In some embodiments, the dosage form of the present invention is a powder-filled pharmaceutical capsule. In some embodiments, the powder is free flowing. In some embodiments, the powder does not contain peanut oil or peanut particles. In some embodiments, the drug in the powder has a mean particle size of about 1 micron to about 15 microns.

In some embodiments, the dosage form of the present invention produces a stable absorption profile for blood plasma levels of progesterone in the subject taking the oral pharmaceutical dosage form.

The present invention is also directed to methods of producing an oral pharmaceutical dosage form. In some embodiments, the method comprises: 1) mixing an aqueous solution of a hydrophilic excipient with an edible oil to form an oil and aqueous mixture; 2) spraying the oil and aqueous mixture onto a powder bed comprising micronized progesterone to form a powder; and 3) encapsulating the powder into an oral capsule. In some embodiments, the powder bed comprises micronized progesterone and is formed in a fluid bed dryer or high shear mixer. In some embodiments, the formed powder is passed through a screen before being encapsulated.

Still other aspects of the present invention include a method of oral progesterone therapy. This method comprises administering the oral dosage form of the present invention to a subject. In some embodiments, the subject is in need of any of the following: 1) hormonal contraception, 2) treatment of secondary amenorrhea, 3) treatment of endometriosis, 4) treatment of luteal phase deficiency, 5) prevention of preterm delivery, 6) treatment of abnormal uterine bleeding due to hormonal imbalance, 7) assisted reproductive techniques, or 8) prevention of endometrial hyperplasia.

The present invention is further directed to kits comprising the oral pharmaceutical dosage form of the present invention. In some embodiments, the kit further comprises printed instructions for its use. In some embodiments, the kit further comprises a printed matter, a pre-recorded media device, or a planner describing the use of the oral pharmaceutical dosage form of the present invention to treat or prevent a condition which could be aided by oral progesterone therapy.

In still other aspects, the present invention provides a method of delivering the oral pharmaceutical dosage form of the present invention, to a patient in need thereof, the method comprising:

(a) registering in a computer readable storage medium the identity of a physician permitted to prescribe the oral pharmaceutical dosage form;

(b) providing the patient with counseling information concerning a risk attendant to the oral pharmaceutical dosage form;

(c) obtaining informed consent of the patient to receive the oral pharmaceutical dosage form despite the risk;

(d) registering the patient in the computer readable medium after obtaining the informed consent; and (e) permitting the patient access to the oral pharmaceutical dosage form.

In some embodiments of this method, the access to the oral pharmaceutical dosage form is a prescription.

In still other aspects, the present invention includes a method of educating a consumer regarding the oral pharmaceutical dosage form of the present invention, the method comprising distributing the oral pharmaceutical dosage form to a consumer with consumer information at a point of sale.

BRIEF DESCRIPTION OF THE DRAWINGS/FIGURES

FIG. 1 depicts an exemplary process that can be used to produce the oral pharmaceutical dosage forms of the present invention.

DETAILED DESCRIPTION OF THE INVENTION

As illustrated by the examples to follow, absorption of progesterone from Prometrium® capsules into systemic circulation within a subject taking the capsule can be erratic.

While most subjects under fasting conditions who take Prometrium® have progesterone blood levels that fall within the desired range, occasionally an individual will show blood levels following a dose of Prometrium® that can be much higher, for example 3- to 7-fold higher. This erratic absorption profile can be present within the same patient from day-to-day as well as between patients.

Prometrium® also exhibits a significant food effect. Specifically, concentrations of progesterone in blood plasma after taking a dose of Prometrium® on a full stomach are much higher, for example 2- to 3-fold higher, than if the same dose was taken on an empty stomach.

High variability in the absorption profile of a progesterone dosage form and a large food effect are undesirable properties. Both instances can lead to higher levels of progesterone in the blood of the subject than desired. These elevated blood levels of progesterone can lead to unwanted side effects, such as sedation. It is unlikely that these surges contribute to the efficacy of dosage forms exhibiting these surges because they do not occur consistently and the short half life of progesterone within the body likely prevents the effects of these surges from lasting more than one day. Therefore, there is a need for an oral capsule formulation containing progesterone that eliminates this erratic absorption profile, thereby reducing unwanted side effects stemming from unnecessarily elevated blood progesterone levels in the patient.

Accordingly, the present invention is directed to an oral pharmaceutical dosage form, methods of making the dosage form, methods of using the dosage form, methods of educating persons about the dosage form, and kits comprising the dosage form; each of which overcome the problems associated with current progesterone products. All these aspects of the present invention are discussed in more detail below. The section headings are provided solely for organizational purposes and are not intended to impart any meaning or division to this document unless specified otherwise.

Oral Pharmaceutical Dosage Forms

The present invention is an oral pharmaceutical dosage form with the unique and unexpected properties of producing blood levels of progesterone in a patient that are consistently within a desired range in contrast to the surges that can arise with use of Prometrium®. The present invention also has a smaller food effect than Prometrium®. This improved absorption profile allows the current invention to have the efficacy of Prometrium® without surges of blood plasma levels of progesterone.

The present invention has other benefits in addition to the more predictable absorption profile. The dosage form of the present invention does not contain peanut oil, making the dosage form suitable for administration to persons who are allergic to peanut oil. In some embodiments, the dosage form of the present invention also uses a powder-filled capsule eliminating the problems associated with leakage of liquid contents from gelatin capsules. The powder-filled capsules have another benefit because they can be broken open and mixed with food, for example applesauce, to assist persons who have difficulty swallowing capsules in taking the dosage form of the present invention.

Some embodiments of the present invention include an oral pharmaceutical dosage form comprising: micronized progesterone, an edible oil, a disintegrant, and a hydrophilic excipient; wherein the dosage form is in a powder form and is contained in a pharmaceutically acceptable capsule. In some embodiments, the disintegrant is crospovidone.

Progesterone is a steroid hormone secreted by the body, for example, by the corpus luteum or placenta. Progesterone can also be chemically synthesized in an identical form to the natural hormone. Progesterone has the following chemical structure:

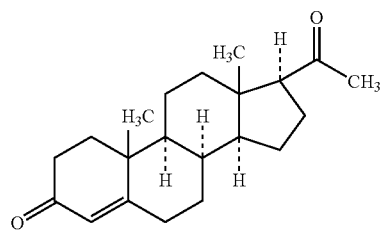

In addition to progesterone, the present invention contemplates the use of other progestins currently known or that will be known to one of skill in the art. These progestins can be used individually or in combination with other progestins, such as progesterone, within the dosage form of the present invention. Suitable progestins for use in the present invention include, but are not limited to, natural and synthetic compounds having progestational activity, such as, for example, progesterone, chlormadinone acetate, norethindrone, cyproterone acetate, norethindrone acetate, desogestrel, levonorgestrel, drospirenone, trimegestone, norgestrel, norgestimate, norelgestromin, etonogestrel, gestodene, and other natural and/or synthetic gestagens.

Prodrugs of suitable progestins can also be used in the dosage forms of the present invention. The expression "prodrug" denotes a derivative of a known direct-acting drug, which derivative has enhanced delivery characteristics and therapeutic value as compared to the drug and is transformed into the active drug by an enzymatic or chemical process. Ethynodiol diacetate, which is converted in vivo to norethindrone, is an example of a progestin prodrug that can be used in the present invention. Additional examples of progestin prodrugs include, but are not limited to, norgestimate (which is converted in vivo to 17-deacetyl norgestimate, also known as norelgestromin), desogestrel (which is converted in vivo to 3-keto-desogestrel, also known as etonogestrel), and norethindrone acetate (which is converted in vivo to norethindrone).

In some embodiments, the progestin used in the present invention is present in a therapeutically effective amount. The term "effective amount" or "therapeutically effective amount," as used herein, refers to the amount of the progestin composition that is effective to achieve its intended purpose after a single dose, wherein a single dose comprises one or more dosage units, or after a course of doses, e.g., during or at the end of the treatment period. Thus, for example, the term "therapeutically effective amount" of the progestin composition, when used in a method of treating endometrial hyperplasia, refers to that dose of the progestin composition that lessens or prevents the occurrence of endometrial hyperplasia when administered to the female in need of such treatment. The therapeutically effective amount will vary depending on the needs of the subject, but this amount can readily be determined by one of skill in the art, for example, a physician.

In some embodiments, the progestin used in the dosage form of the present invention can be micronized. As used herein, "micronized" means that the particles of the composition have been reduced to particles that are only a few microns or less in diameter. For example, micronized progesterone means that the progesterone particles have been reduced in size such that they are only a few microns or less in diameter.

In some embodiments, the micronized progesterone is present in an amount ranging from about 1% to about 95% of the weight of the capsule contents. As used herein, "capsule contents" refers to the ingredients which are placed inside the capsule shell and subsequently encapsulated within the shell. In some embodiments, the micronized progesterone is present in an amount ranging from about 20% to about 70% of the weight of the capsule contents. In some embodiments, the amount of micronized progesterone is present in an amount ranging from about 40% to about 60% of the weight of the capsule contents. In some embodiments, the amount of micronized progesterone in the capsule contents is about 55% by weight of the capsule contents.

In some embodiments, the oral dosage form of the present invention contains a dose of about 10 mg to about 500 mg of micronized progesterone. In some embodiments, the oral dosage form contains a dose of about 100 mg of micronized progesterone. In some embodiments, the oral dosage form contains a dose of about 200 mg of micronized progesterone. In some embodiments, the oral dosage form contains a dose of about 300 mg of micronized progesterone. In some embodiments, the oral dosage form contains a dose of about 400 mg of micronized progesterone. In some embodiments, the oral dosage form contains a dose of about 500 mg of micronized progesterone.

The oral dosage form of the present invention also includes an edible oil. As used herein, an "edible oil" is any oil which can be safely consumed by a mammal. These oils will generally be selected from those oils generally regarded as safe for pharmaceutical or culinary use. Suitable edible oils for the present invention include, but are not limited to, safflower oil, linseed oil, soybean oil, corn oil, sunflower oil, sesame oil, olive oil, cottonseed oil, flaxseed oil, menhaden oil, and mixtures thereof. The dosage forms of the present invention can also use any other edible oil that is currently known or will be known to one of skill in the art with the exception of peanut oil.

In some embodiments, the edible oil is present in an amount ranging from about 1% to about 95% of the weight of the capsule contents. In some embodiments, the edible oil is present in an amount ranging from about 5% to about 25% of the weight of the capsule contents. In some embodiments, the edible oil is present in an amount ranging from about 10% to about 15% of the weight of the capsule contents. In some embodiments, the edible oil is about 11% of the capsule contents.

The oral dosage form of the present invention also includes a disintegrant. As used herein, a "disintegrant" is a substance that has the ability to absorb oil or lipid materials to maintain the free-flowing property of the formulation despite a high percentage of low melting point oils or lipids in the formulation. Disintegrants include, but are not limited to, starches, clays, celluloses, algins, gums, and cross-linked polymers, including, e.g., crospovidone, sodium starch glycolate, croscarmellose, methylcellulose, agar, bentonite, cellulose and wood products, natural sponge, cation-exchange resins, alginic acid, guar gum, citrus pulp, carboxymethylcellulose, and combinations thereof.

In some embodiments of the present invention, crospovidone is present in the capsule contents. Crospovidone is a water-insoluble, synthetic, cross-linked homopolymer of N-vinyl-2-pyrrolidinone. Cross-linked polyvinylpyrrolidone (crospovidone), NF is available under the trade name POLYPLASDONE® XL (ISP Technologies, Wayne, N.J.).

In some embodiments, crospovidone is present in an amount ranging from about 1% to about 95% of the weight of the capsule contents. In some embodiments, crospovidone is present in an amount ranging from about 5% to about 25% of the weight of the capsule contents. In some embodiments, crospovidone is present in an amount ranging from about 10% to about 20% of the weight of the capsule contents. In some embodiments, crospovidone is about 15% of the weight of the capsule contents.

In some embodiments, the oral dosage of the present invention includes a hydrophilic excipient. As used herein, the term "hydrophilic excipient" means an excipient or a mixture of excipients which can be classified as hydrophilic, i.e. compounds that dissolve easily in water. As used herein, the term "excipient" refers to the additives used to convert an active compound into a form suitable for its intended purpose. For compositions of the present invention suitable for administration to humans, the term "excipient" is meant to include, but is not limited to, those ingredients described in *Remington: The Science and Practice of Pharmacy*, Lippincott Williams & Wilkins, 19th ed. (1995) (hereinafter Remington's), which is herein incorporated by reference in its entirety.

Suitable hydrophilic excipients for the present invention include Avicel® (microcrystalline cellulose), corn starch, potato starch, pregelatinized starch, povidone, polysorbate, mannitol, sodium starch glycolate, and mixtures thereof. The dosage forms of the present invention can also use any other hydrophilic excipient that is currently known or will be known to one of skill in the art.

In some embodiments, the hydrophilic excipient is present in an amount ranging from about 1% to about 95% of the weight of the capsule contents. In some embodiments, the hydrophilic excipient is present in an amount ranging from about 5% to about 50% of the weight of the capsule contents. In some embodiments, the hydrophilic excipient is present in an amount ranging from about 10% to about 25% of the weight of the capsule contents. In some embodiments, the hydrophilic excipient is about 15% of the capsule contents.

In some embodiments, the dosage forms of the present invention can further comprise an absorbant. Suitable absorbants include Syloid® (W.R. Grace & Co., Columbia, Md.), silicon dioxide and its derivatives, micronized silicas, lactose, lactose monohydrate, methylcellulose, microcrystalline cellulose, sugars, maltodextrin, and mixtures thereof. The dosage forms of the present invention can also use any other absorbant that is currently known or will be known to one of skill in the art.

In some embodiments, the dosage forms of the present invention can further comprise an antioxidant. Suitable antioxidants include adipic acid, alpha lipoic acid, ascorbyl palmitate, biotin, boron, butylated hydroxyl toluene, butylated hydroxyanisole, carotenoids, calcium citrate, sodium metabisulfate, tocopherols, and mixtures thereof. The dosage forms of the present invention can also use any other oil-miscible antioxidant that is currently known or will be known to one of skill in the art.

In some embodiments, the dosage forms of the present invention can further comprise a lubricant. Suitable lubricants include magnesium stearate, colloidal silicon dioxide, silica gel, aluminum stearate, talc, stearic acid, sodium stearate, calcium stearate, sodium stearyl fumarate, and mixtures thereof. The dosage forms of the present invention can also use any other lubricant suitable for pharmaceutical dosage forms that is currently known or will be known to one of skill in the art.

In some embodiments, the dosage form of the present invention is encapsulated.

The encapsulation of medicinal agents remains a popular alternative to tablets or other methods of administering drugs. Capsules have numerous advantages, for example, they are tasteless, easily administered, and easily filled in large quantities commercially. Moreover, some people find it easier to swallow capsules than tablets and therefore prefer to take capsules whenever possible. Capsules come in two basic types, the hard gelatin capsule or the soft elastic capsule.

The hard gelatin capsule, also referred to as the dry-filled capsule (DFC), consists of two sections. These two sections, the body and cap, slip over one another to form a sealed capsule. After the hard gelatin capsules have been filled and the cap has been applied, the capsule can be spot-welded or banded with molten gelatin at the seam to seal the capsule. This prevents the capsules from coming apart if subjected to vibration or rough handling, for example, as may occur during high speed counting processes or during packaging. Another approach used to solve capsule breakage is to use locking rings formed in both the cap and body to seal the capsule.

The soft elastic capsule is a soft, globular, gelatin shell that is thicker than the shell of hard gelatin capsules. The gelatin can be plasticized by adding, for example, glycerin, sorbitol, or a similar polyol to form soft elastic capsules. This dosage form can be used with formulations where the suspending vehicle or solvent is an oil. However, the contents can be a liquid, powder, paste, or other form. These capsules are sealed at the seam to prevent them from breaking open prematurely.

Either capsule type is available in multiple sizes. These sizes range from 000 to 5 as described in Remington's. The appropriate capsule size is readily determined by one of skill in the art depending on the amount and volume of medicine, e.g. the number of milligrams and volume of medicine in the capsule, to be delivered to the person taking the capsule.

In some embodiments, the dosage forms of the present invention are powder-filled pharmaceutical capsules. In some embodiments, the powder is free flowing. Further, the powder does not contain peanut oil or peanut particles. In some embodiments, the drug in the powder has a mean particle size of about 1 micron to about 15 microns. The term "particle size" refers to the particle diameter. As used herein, the term "diameter" is a volumetric measurement based on the presumed spherical shape of the drug particles. As used herein, the term "mean diameter," when used in reference to the size of drug particles, refers to the sum of the diameter measurements of all measurable particles measured, divided by the total number of particles measured. As used herein, the term "median diameter," when used in reference to the size of drug particles, indicates that about 50% of all measurable particles measured have a particle diameter less than the defined median particle diameter value, and that about 50% of all measurable particles measured have a particle diameter greater than the defined median particle diameter value. In some embodiments the powder comprises particulate matter in the form of beads for pharmaceutical delivery of the drug.

In some embodiments, the present invention provides progesterone compositions having a desirable pharmacokinetic profile when orally administered to a subject, e.g., a female. The desirable pharmacokinetic profile, relative to the pharmacokinetic profile of Prometrium®, can include one or more of the following characteristics: 1) more consistent blood plasma levels of progesterone in the subject; 2) less variance in the $AUC_{(0-T)}$ for progesterone in each subject from day to day; 3) less variance in the $AUC_{(0-T)}$ for progesterone between subjects, 4) less variance in the $C_{max}$ for progesterone in each subject from day to day, 5) less variance in the $C_{max}$ for progesterone between subjects, or 6) a smaller food effect.

To determine the pharmacokinetic profile of a dosage form, for example, the dosage form of the present invention, the dosage form can be administered to a postmenopausal woman under fasting conditions. Then at specified time points, e.g., at 0, 0.5, 1, 1.5, 2, 2.5, 3, 3.5, 4, 5, 6, 7, 8, 9, 10, 11, 12, 13, 14, 15, 16, 17, 18, 19, 20, 21, 22, 23, and 24 hours after administering the dosage form, progesterone in plasma levels are obtained. The progesterone in plasma levels can be analyzed using a highly selective LC-MS-MS method with a limit of quantitation of 0.1 ng/mL.

In some embodiments, the $AUC_{(0-T)}$ does not exceed 250 ng*hr/mL when a 400 mg dose of micronized progesterone is administered under fasting conditions to a subject, e.g., where the subject is an average, healthy, adult postmenopausal North American woman with a normal Body Mass Index. Body Mass Index (BMI) is a measure of an individual's weight scaled to their height. Currently, a North American adult individual with a BMI under 18.5 kg/m² is considered underweight, 18.5-24.9 kg/m² is normal weight, 25-29.9 kg/m² is overweight, and 30 kg/m² or more is obese. See, e.g., James, P. T. et al., *Obes. Res.* 9(Suppl. 4): 228S-233S (2001). In some other embodiments, the $AUC_{(0-T)}$ does not exceed 200 ng*hr/mL when a 400 mg dose of micronized progesterone is administered under fasting conditions to a subject, e.g., where the the subject is an average, healthy, adult postmenopausal North American woman with a normal Body Mass Index. In still other embodiments, the $AUC_{(0-T)}$ does not exceed 150 ng*hr/mL when a 400 mg dose of micronized progesterone is administered under fasting conditions to a subject, e.g., where the subject is an average, healthy, adult postmenopausal North American woman with a normal Body Mass Index.

In some embodiments, the $AUC_{(0-T)}$ does not exceed 200 ng*hr/mL when a 200 mg dose of micronized progesterone is administered under fasting conditions to a subject, e.g., where the subject is an average, healthy, adult postmenopausal North American woman with a normal Body Mass Index. In some other embodiments, the $AUC_{(0-T)}$ does not exceed 175 ng*hr/mL when a 200 mg dose of micronized progesterone is administered under fasting conditions to a subject, e.g., where the subject is an average, healthy, adult postmenopausal North American woman with a normal Body Mass Index. In still other embodiments, the $AUC_{(0-T)}$ does not exceed 150 ng*hr/mL when a 200 mg dose of micronized progesterone is administered under fasting conditions to a subject, e.g., where the subject is an average, healthy, adult postmenopausal North American woman with a normal Body Mass Index.

In some embodiments, the $AUC_{(0-T)}$ does not exceed 100 ng*hr/mL when a 100 mg dose of micronized progesterone is administered under fasting conditions to a subject, e.g., where the subject is an average, healthy, adult postmenopausal North American woman with a normal Body Mass Index. In some other embodiments, the $AUC_{(0-T)}$ does not exceed 90 ng*hr/mL when a 100 mg dose of micronized progesterone is administered under fasting conditions to a subject, e.g., where the subject is an average, healthy, adult postmenopausal North American woman with a normal Body Mass Index. In still other embodiments, the $AUC_{(0-T)}$ does not exceed 80 ng*hr/mL when a 100 mg dose of micronized progesterone is administered under fasting conditions to a subject, e.g., where the subject is an average, healthy, adult postmenopausal North American woman with a normal Body Mass Index.

In some embodiments, the $AUC_{(0-T)}$ is about 5 to about 115 ng*hr/mL with a coefficient of variation of about 90 when a 400 mg dose of micronized progesterone is administered to a subject, e.g., where the subject is an average, healthy, adult postmenopausal North American woman with a normal Body Mass Index. In other embodiments, the $AUC_{(0-T)}$ is about 1 to about 135 ng*hr/mL with a coefficient of variation of about 140 when a 200 mg dose of micronized progesterone is administered to a subject, e.g., where the subject is an average, healthy, adult postmenopausal North American woman with a normal Body Mass Index. In still other embodiments, the $AUC_{(0-T)}$ is about 1 to about 80 ng*hr/mL with a coefficient of variation of about 140 when a 100 mg dose of micronized progesterone is administered to a subject, e.g., where the subject is an average, healthy, adult postmenopausal North American woman with a normal Body Mass Index.

In some embodiments, the $C_{max}$ does not exceed 60 ng/mL when a 400 mg dose of micronized progesterone is administered to a subject. In some other embodiments, the $C_{max}$ does not exceed 50 ng/mL when a 400 mg dose of micronized progesterone is administered to a subject. In still other embodiments, the $C_{max}$ does not exceed 45 ng/mL when a 400 mg dose of micronized progesterone is administered to a subject.

In some embodiments, the $C_{max}$ does not exceed 60 ng/mL when a 200 mg dose of micronized progesterone is administered to a subject. In some other embodiments, the $C_{max}$ does not exceed 50 ng/mL when a 200 mg dose of micronized progesterone is administered to a subject. In still other embodiments, the $C_{max}$ does not exceed 45 ng/mL when a 200 mg dose of micronized progesterone is administered to a subject.

In some embodiments, the $C_{max}$ does not exceed 45 ng/mL when a 100 mg dose of micronized progesterone is administered to a subject. In some other embodiments, the $C_{max}$ does not exceed 35 ng/mL when a 100 mg dose of micronized progesterone is administered to a subject. In still other embodiments, the $C_{max}$ does not exceed 30 ng/mL when a 100 mg dose of micronized progesterone is administered to a subject.

In some embodiments, the $C_{max}$ is about 1 to about 45 ng/mL with a coefficient of variation of about 107 when a 400 mg dose of micronized progesterone is administered to a subject. In other embodiments, the $C_{max}$ is about 1 to about 43 ng/mL with a coefficient of variation of about 158 when a 200 mg dose of micronized progesterone is administered to a subject. In still other embodiments, the $C_{max}$ is about 1 to about 30 ng/mL with a coefficient of variation of about 168 when a 100 mg dose of micronized progesterone is administered to a subject.

Methods of Making the Oral Dosage Forms

The oral dosage forms of the present invention can be prepared and filled using large scale production methods. Suitable methods include extemporaneous filing methods and machine filing methods as disclosed in Remington's.

In some embodiments, a dosage form is made using a method comprising: 1) mixing an aqueous solution of a hydrophilic excipient with an edible oil to form an oil and aqueous mixture; 2) spraying the oil and aqueous mixture onto a powder bed comprising micronized progesterone to form a powder; and 3) encapsulating the powder into an oral capsule.

In some embodiments, the powder bed comprises micronized progesterone and is formed in a fluid bed dryer or high shear mixer. In some embodiments, the formed powder is passed through a screen before being encapsulated.

Methods of Using the Oral Dosage Forms

The present invention is directed to methods of oral progestin therapy. As used herein, "subject" includes any mammal in need of progestin therapy. As used herein, "female" refers to any animal classified as a mammal, including humans and non-humans, such as, but not limited to, domestic and farm animals, zoo animals, sports animals, and pets.

"Peri-menopausal female" refers to a woman who has not yet definitely arrived at menopause but who is experiencing symptoms or signs associated with menopause. "Peri-menopause" means "about or around the time of menopause." It encompasses the years preceding the last menstrual period during which ovarian function declines and ultimately ceases and can include the presence of symptoms or signs and irregular cycles. "Menopausal female" refers to a woman who has definitely arrived at menopause and may be experiencing symptoms or signs associated with menopause. Menopause or post-menopause is the permanent cessation of menstruation after the loss of ovarian activity and is generally defined clinically as the absence of menstruation for about one year. Menopause may occur naturally in a woman or it may be artificially induced, e.g., through surgical or chemical means. For example, removal of the ovaries, which can occur, e.g., through hysterectomy, frequently leads to symptoms or signs associated with menopause ("surgical menopause").

The terms "treat" and "treatment" refer to both therapeutic treatment and prophylactic or preventative measures, wherein the object is to prevent or slow down (lessen) an undesired physiological condition, disorder, or disease, or to obtain beneficial or desired clinical results. For purposes of this invention, beneficial or desired clinical results include, but are not limited to, alleviation of the symptoms or signs associated with a condition, disorder, or disease; diminishment of the extent of a condition, disorder, or disease; stabilization of a condition, disorder, or disease (i.e., where the condition, disorder, or disease is not worsening); delay in onset or progression of the condition, disorder, or disease; amelioration of the condition, disorder, or disease state; remission (whether partial or total and whether detectable or undetectable) of the condition, disorder, or disease; or enhancement or improvement of a condition, disorder, or disease. Treatment includes eliciting a clinically significant response without excessive side effects. Treatment also includes prolonging survival as compared to expected survival if not receiving treatment.

As used herein, "about" refers to plus or minus 10% of the indicated number. For example, "about 200 μm" indicates a range of 180 μm to 220 μm; "about 10%" indicates a range of 9% to 11%.

The term "continuous" or "consecutive" in reference to "administration" means that the frequency of administration is at least once daily. Note, however, that the frequency of administration can be greater than once daily and still be "continuous," e.g., twice or even three times daily, as long as the dosage levels as specified herein are not exceeded.

The term "dosage level" means the total amount of progesterone administered per day. Thus, for example, "continuous administration" of progesterone to a woman at a "dosage level" of 400 mg means that the woman receives a total of 400 mg of progesterone on a daily basis, whether the progesterone is administered as a single 400 mg dose or, e.g., two separate 200 mg doses. A conventional means of continuously administering progesterone is as a single daily oral dose at the prescribed dosage level.

The present invention further encompasses a method of contraception which comprises orally administering to a female of child bearing age the pharmaceutical dosage form of the present invention. As used herein, "hormonal contraception" means administering a dosage form containing a hormone, e.g. progesterone, to a female capable of becoming pregnant to prevent the female from becoming pregnant.

Hormonal methods of contraception are very reliable and reversible once treatment is stopped. The most popular hormonal contraception is a small tablet that usually contains a combination of estrogen and progesterone. Alternatives to the latter include patches, injections, and implants. For women who cannot take estrogen, or for those who wish to avoid estrogen, treatment with only a progestin is an alternative, such as treatment with a progestin-only tablet. In such cases, a progestin-only tablet is taken continuously without a break. The female taking a contraceptive can be, for example, of childbearing age or peri-menopausal.

In some embodiments, the dosage form of the present invention can be used in a progestin-only method of contraception. In some embodiments, the oral pharmaceutical dosage form will be a progesterone-only dosage form. As used herein, a "progesterone-only dosage form" is a dosage form that comprises natural or synthetic progesterone but does not contain a therapeutically effective amount of any other hormone capable of use for hormonal contraception. In these embodiments, the progesterone-only dosage form delivers a daily dosage of about 0.1 mg to about 1.0 mg of progesterone to a female. In these embodiments, the progesterone-only dosage form can be taken continuously. The present invention also contemplates kits comprising a progesterone-only dosage form.

In some embodiments, the dosage form of the present invention can be used in a method of hormonal contraception involving a progestin in combination with another hormone. In these embodiments, the oral pharmaceutical dosage form will comprise a progestin and another hormone, e.g. an estrogen, which can be used in hormonal contraception. In some of these embodiments, the dosage form delivers a daily dosage of 0.1 mg to 1 mg daily of a progestin, e.g. progesterone, to a female in combination with a dosage of another hormone. Other hormones that can be used in this invention include an estrogen, a conjugated estrogen, a selective estrogen receptor modulator, or a progestin. In these embodiments, the dosage form can be taken continuously or cyclically. The present invention also contemplates kits comprising a dosage form comprising a progestin in combination with another hormone.

Suitable estrogens in the present invention include, but are not limited to, natural and synthetic compounds having estrogenic activity such as, for example, estradiol (17β-estradiol); 17α-estradiol; estriol; estrone; esters of estradiol (17β-estradiol), 17α-estradiol, estriol, and estrone (for example, the acetate, sulfate, valerate, or benzoate esters of these compounds such as estradiol 17β-cypionate, estradiol 17-propionate, estradiol 3-benzoate, and piperazine estrone sulfate); ethinyl estradiol; conjugated estrogens (natural and synthetic); mestranol; agonistic anti-estrogens; selective estrogen modulators; and mixtures thereof.

Prodrugs of suitable estrogens can also be used in the extended cycle regimen of the present invention. Examples of estrogen prodrugs that can be used in the present invention include, but are not limited to, estradiol acetate (which is converted in vivo to 17β-estradiol) and mestranol (which is converted in vivo to ethinyl estradiol).

Suitable conjugated estrogens for use in the present invention include, but are not limited to, natural and synthetic compounds having estrogenic activity, such as, for example, estrone sulfate, equilin sulfate, 17α-dihydroequilin sulfate, 17α-estradiol sulfate, 17β-dihydroequilin sulfate, 17α-dihydroequilenin sulfate, 17β-dihydroequilenin sulfate, 17β-estradiol sulfate, $\Delta^{8,9}$-dehydroestrone sulfate, equilenin sulfate, and mixtures thereof. In some embodiments, the sodium salt of the conjugated estrogen can be used.

Suitable selective estrogen receptor modulators for the present invention include, but are not limited to, natural and synthetic compounds whose estrogenic activities are tissue selective, such as, for example, raloxifene, tamoxifene, toremifene, and mixtures thereof.

In some embodiments, an additional pharmaceutical agent can be administered as part of the methods of hormonal contraception of the current invention. Examples of other pharmaceutically active agents that can be administered using the contraceptive methods of the invention include, but are not limited to, one or more of the B complex vitamins, such as vitamin B3 (niacin (i.e., nicotinic acid and/or nicotinamide)), vitamin B9 (folic acid or folate), vitamin B6 and/or vitamin B12; iron; bisphosphonates (e.g., alendronate); and teriparatide (e.g., FORTEO™).

The dosage forms of the present invention can be used to treat secondary amenorrhea. Secondary amenorrhea is a condition in which menstruation begins at the appropriate age, but later ceases for 6 or more months in the absence of normal causes such as pregnancy, lactation, or menopause. The present invention provides a method of treating secondary amenorrhea by administering the dosage form of the present invention to a female in need thereof.

The present invention is drawn to a method of treating endometriosis in a female in need thereof, the method comprising administering to the female a pharmaceutical dosage form of the present invention. The female can be, but is not limited to, a female of childbearing age or a peri-menopausal female.

In hormonal treatment of endometriosis, endometriotic tissue responds to adverse endocrine environments (low estrogen and/or high progestin concentration). Progestins produce marked atrophy of the endometrium and ectopic endometrial tissue and decrease intraperitoneal inflammation associated with endometriosis. The American College of Obstetrics and Gynecology stated that progestins, alone or in combination with estrogens as oral contraceptives, are an optimal choice for the management of endometriosis in women who desire contraception (American College of Obstetricians and Gynecologists, *ACOG Practice Bulletin No.* 11 (December 1999)). Because pain associated with endometriosis is often episodic and related to uterine bleeding, the use of the dosage form according to the present invention of the present invention is beneficial for treating endometriosis.

The invention is further drawn to a method of reducing the risk of endometrial cancer in a female in need thereof by administering to the female a dosage form according to the present invention. The female can be, for example, of childbearing age, peri-menopausal, or menopausal. The invention is also drawn to a method of providing contraception and reducing the risk of endometrial cancer in a female in need thereof by administering to the female a dosage form according to the present invention. The female can be, for example, a female of childbearing age or peri-menopausal.

Luteal phase deficiency (LPD) is characterized by inadequate secretory transformation of the endometrium, resulting from recurrent deficiencies in progesterone production. (Soules, M R et al., *Luteal Phase Deficiency: Characterization of Reproductive Hormones Over the Menstrual Cycle, J. Clin. Endo. & Metab.*, Vol 69, 804-812 (1989).) LPD has been implicated in both infertility and recurrent pregnancy loss. The present invention is drawn to a method of treating luteal phase deficiency in a female in need thereof, the method comprising administering to the female a pharmaceutical dosage form of the present invention.

The present invention is drawn to a method of treating preterm delivery in a female in need thereof, the method comprising administering to the female a pharmaceutical dosage form of the present invention. The female can be, but is not limited to, a female considered at risk for preterm delivery. A female can be considered at risk for preterm delivery if she has previously given birth to a child preterm or if other conditions indicate she may have a preterm delivery.

The present invention is drawn to a method of treating irregular bleeding due to a hormonal imbalance in a female in need thereof, the method comprising administering to the female a pharmaceutical dosage form of the present invention.

The present invention is drawn to a method of aiding assisted reproductive techniques, for example, in vitro fertilization, in a female in need thereof, the method comprising administering to the female a pharmaceutical dosage form of the present invention. As used herein, "assisted reproductive technique" encompasses any currently known or later discovered technique designed to assist a mammal in having a child who otherwise might not be able to have a child.

The present invention is further drawn to methods of preventing endometrial hyperplasia. The vast majority of women taking continuous low-dose estrogen will not have bleeding for many months or even years; however, there is a distinct risk posed by this routine of silently (i.e., exhibiting no overt symptoms or signs) developing "hyperplasia of the endometrium." The latter term refers to an overstimulation of the lining of the uterus, which can become pre-malignant, coupled with the possibility that the patient will eventually develop cancer of the uterine lining even under such a low-dose regimen (Gusberg et al., *Obstetrics and Gynaecology* 17:397-412 (1961)).

The addition of progestin, as in a dosage form according to the present invention, will virtually eliminate the concern about developing endometrial hyperplasia and reduce the risk of developing endometrial carcinoma below that of the untreated general population. Suitable estrogens that can be combined with progesterone for use in the present invention include, but are not limited to, natural and synthetic compounds having estrogenic activity, such as, for example, estradiol (17β-estradiol); 17α-estradiol; estriol; estrone; esters of estradiol (17β-estradiol), 17α-estradiol, estriol, and estrone (for example the acetate, sulfate, valerate or benzoate esters of these compounds such as estradiol 17β-cypionate, estradiol 17-propionate, estradiol 3-benzoate, and piperazine estrone sulfate); ethinyl estradiol; conjugated estrogens (natural and synthetic); mestranol; agonistic anti-estrogens; selective estrogen receptor modulators; and mixtures thereof.

The present method of oral progesterone therapy can also be used to treat any condition presently known, or that will be known, to one of skill in the art for which progesterone therapy could mitigate or diminish at least one symptom of the condition.

Kits Comprising the Oral Dosage Form

In addition to any kit mentioned previously, the invention also provides kits comprising the oral pharmaceutical dosage form of the present invention. These kits can include one or more containers filled with one or more of the ingredients of the oral pharmaceutical dosage forms of the invention.

In some embodiments, the kit comprises a container for the dosage form of the present invention. Suitable containers include, for example, a bottle, a box, a blister card, a foil packet, or a combination thereof. Optionally, the kit also contains directions for properly administering the dosage form. The kits can also be designed in a manner such that they are tamper resistant or designed to indicate if tampering has occurred. Optionally, the kit of the present invention can contain the dosage form of the present invention in combination with another pharmaceutical composition.

Optionally associated with the container(s) in the kits of the present invention can be a notice or printed instructions. Such printed instructions can be in a form prescribed by a governmental agency regulating the manufacture, use, or sale of pharmaceuticals or biological products, which notice reflects approval by the agency of the manufacture, use, or sale for human administration to treat a condition that could be treated by oral progesterone therapy. In some embodiments, the kit further comprises printed matter, which, e.g., provides information on the use of the dosage form to treat a condition or disease or a pre-recorded media device which, e.g., provides information on the use of the dosage form to treat a condition or disease, or a planner.

"Printed matter" can be, for example, one of a book, booklet, brochure or leaflet. The printed matter can describe the use of the dosage form of the present invention to treat a condition or disease. Possible formats include, but are not limited to, a bullet point list, a list of frequently asked questions (FAQ) or a chart. Additionally, the information to be imparted can be illustrated in non-textual terms using pictures, graphics, or other symbols.

"Pre-recorded media device" can be, for example, a visual media device, such as a videotape cassette, a DVD (digital video disk), filmstrip, 35 mm movie, or any other visual media device. Alternately, pre-recorded media device can be an interactive software application, such as a CD-ROM (compact disk-read only memory) or floppy disk. Alternately, pre-recorded media device can be, for example, an audio media device, such as a record, audiocassette, or audio compact disk. The information contained on the pre-recorded media device can describe the use of the dosage form of the present invention to treat a condition or disease.

A "planner" can be, for example, a weekly, a monthly, a multi-monthly, a yearly, or a multi-yearly planner. The planner can be used as a diary to monitor dosage amounts, to keep track of dosages administered, or to prepare for future events wherein taking a regularly administered dosage form of the present invention can be difficult. Alternately, the planner can be a calendar which will provide a means to monitor when a dosage has been taken and when it has not been taken. This type of planner will be particularly useful for patients having unusual schedules for administering medication to themselves. Additionally, the planner can be useful for the elderly, children, or other patient group who may administer medication to themselves and may become forgetful. One skilled in the art will appreciate the variety of planning tools that would be appropriate for use with the present invention.

The kit can also include a container for storing the other components of the kit. The container can be, for example, a bag, box, envelope or any other container that would be suitable for use in the present invention. Preferably, the container is large enough to accommodate each component and/or any administrative devices that may be accompany the dosage form of the present invention. However, in some cases, it may be desirable to have a smaller container which can be hidden in a patient's pocketbook, briefcase, or pocket.

In some embodiments, the present invention includes a kit comprising the oral pharmaceutical dosage form of the present invention. In some embodiments, the kit further comprises printed instructions for its use. In some embodiments, the kit further comprises a printed matter, a pre-recorded media device, or a planner describing the use of the oral pharmaceutical dosage form of the present invention to treat or prevent a condition which could be aided by oral progesterone therapy.

In some aspects, the present invention provides a method of delivering the oral pharmaceutical dosage form of the present invention, to a patient in need thereof, the method comprising:

(a) registering in a computer readable storage medium the identity of a physician permitted to prescribe the oral pharmaceutical dosage form;

(b) providing the patient with counseling information concerning a risk attendant to the oral pharmaceutical dosage form;

(c) obtaining informed consent of the patient to receive the oral pharmaceutical dosage form despite the risk;

(d) registering the patient in the computer readable medium after obtaining the informed consent; and (e) permitting the patient access to the oral pharmaceutical dosage form.

In some embodiments of this method, the access to the oral pharmaceutical dosage form is a prescription.

Still other aspects of the present invention include a method of educating a consumer regarding the oral pharmaceutical dosage form of the present invention, the method comprising distributing the oral pharmaceutical dosage form to a consumer with consumer information at a point of sale.

In some embodiments, the consumer information is presented in a format selected from the group consisting of: English language text, a foreign language text, a visual image, a chart, a telephone recording, a website, and access to a live customer service representative. In some embodiments, the consumer information is a direction for use, appropriate age use, indication, contraindication, appropriate dosing, warning, telephone number, or website address.

In some embodiments, the method of educating the consumer further comprises providing professional information to a relevant person in a position to answer a consumer question regarding the oral pharmaceutical dosage form. In some embodiments, the relevant person is a physician, physician assistant, nurse practitioner, pharmacist, or customer service representative.

In some embodiments, the distributing of the oral pharmaceutical dosage form is to a location with a pharmacist or a health care provider.

Having generally described this invention, a further understanding can be obtained by reference to the examples provided herein. These examples are for purposes of illustration only and are not intended to be limiting.

EXAMPLES

Example 1

Progesterone capsules were prepared by the process illustrated in FIG. 1.

Povidone, polysorbate, and water were mixed in a stainless steel container until it formed a clear solution. In another stainless steel container, safflower oil, butylated hydroxyl toluene (BHT), and vitamin E acetate were mixed until it formed a clear solution. Then, the oil dispersion was mixed with the aqueous solution using an air-operated mixer.

A fluid bed dryer was then loaded with crospovidone NF, progesterone USP micronized, and lactose monohydrate NF to form a powder bed. The previously prepared oil dispersion and aqueous solution mixture was then sprayed onto the powder bed. The resulting powder was then passed through a Quadro®Comil® screen and then mixed with crospovidone. Then, Cab-O-Sil® and magnesium stearate were mixed in and then the resulting powder was passed through a No. 30 screen. The powder was then encapsulated in an acceptable pharmaceutical capsule, for example, a hard gelatin capsule.

Example 2

Using the process described in Example 1 and FIG. 1, the oral dosage forms of some embodiments of the present invention displayed in Table 1 can be prepared.

TABLE 1

Formulation Compositions for Progesterone 100 MG, 200 MG and 300 MG Capsules

| Composition | Formulation A | Formulation B | Formulation C |
|---|---|---|---|
| Progesterone, USP - Micronized (mg) | 100 | 200 | 300 |
| Lactose monohydrate, NF (mg) | 15.275 | 30.55 | 45.825 |
| Povidone, USP (Plasdone K ®-29-32) (mg) | 15 | 30 | 45 |
| Purified water, USP** (mg) | — | — | — |
| Polysorbate 80, NF (mg) | 0.15 | 0.3 | 0.45 |
| Crospovidone, NF (Polyplasdone ® XL) (mg) | 27.5 | 55.3 | 82.95 |
| Safflower oil, USP (mg) | 20 | 40 | 60 |
| Butylated hydroxytoluene, food grade (Tenox ® BHT) (mg) | 0.10 | 0.2 | 0.3 |
| Vitamin E, USP (dl-alpha tocopheryl acetate) (mg) | 0.25 | 0.5 | 0.75 |
| Colloidal silicon dioxide, NF (Cab-O-Sil ®) (mg) | 0.075 | 0.15 | 0.225 |
| Magnesium stearate, NF (mg) | 1.5 | 3 | 4.5 |
| Capsule size | #2 | #1 | #0 |
| Total (mg) | 180 | 360 | 540 |

**Not a part of the finished product.

Example 3

Dosage forms of the present invention were administered to subjects in a randomized, 5-way crossover dose proportionality study. The subjects were healthy postmenopausal adult females. The study objectives, design, and methodology are provided below. In addition, Tables 2-5 illustrate some of the results obtained in this study. These tables include data for the capsules of the present invention at 100 mg (Formulation A in Tables 2 and 3), 200 mg (Formulation B in Tables 4 and 5), and 400 mg (Formulation B at 2×200 mg in Tables 2 and 3) doses in addition to data for the Prometrium® capsules at 200 mg (Tables 2 and 3) and 400 mg (Tables 2 and 3) doses.

Objective

The primary objective of this study was to assess the dose proportionality of single 100 mg, 200 mg, and 400 mg doses of progesterone capsules of the present invention following administration under testing conditions.

The secondary objectives of this study were:

To assess, for comparative purposes, the dose proportionality of single 100 mg and 400 mg doses of 100 mg and 2×200 mg Prometrium® capsules following administration under fasting conditions; and To evaluate, for information purposes, the relative bioavailability of the progesterone capsules of the present invention compared to 100 mg and 2×200 mg Prometrium® capsules under fasting conditions.

Study Design

This was an open-label, randomized, single-dose, 5-way crossover, dose proportionality study performed on 30 healthy postmenopausal non-smoking female volunteers. A total of 29 subjects completed the clinical phase of the study. In each period, subjects were housed from at least 20 hours before dosing until after the 24-hour blood draw. There was a 7-day washout between each period.

Methods

The $AUC_{(0-T)}$, $AUC_{inf}$, $AUC/AUC_{inf}$, $C_{max}$, $t_{max}$, half-life, and kel pharmacokinetic parameters were calculated for progesterone in plasma.

To assess dose proportionality for the Test (100 mg Formulation A and 400 mg Formulation B) and Reference (100 mg and 400 mg Prometrium®) products, a statistical linear relationship between the ln-transformed pharmacokinetic parameters $AUC_{(0-T)}$ and $C_{max}$ of plasma progesterone and the ln-transformed dose were fitted by using an extension of the analysis of variance (ANOVA) model. The analysis was performed separately for the test and reference products. The model included sequence and period as fixed effects, subject nested within sequence as a random effect, and ln-transformed dose as a covariate. As a first step, the statistical linear relationship between the ln-transformed pharmacokinetic parameters and the ln-transformed dose were verified by including the (indose)² term in the model to test the quadratic effect at a 5% level of significance. For the test products, the statistical linear relationship was concluded if the quadratic term was not statistically significant. The first step was not applicable for the reference product, where only two different doses (100 mg and 400 mg) were available. The statistical linear relationship was assumed for the reference product. If the statistical linear relationship was established in the first step, then a second step was performed. As a second step, the 95% confidence intervals for the slope of the ln-transformed pharmacokinetic parameters for plasma progesterone were calculated.

To evaluate the relative bioavailability of the progesterone capsules of the present invention at 100 mg (Formulation A) and 2×200 mg (Formulation B) dosage levels as compared to Prometrium® at 100 mg and 2×200 mg dosage levels under fasting conditions, an ANOVA including sequence, formulation and period as fixed effects and subject nested within sequence as a random effect, was performed on the ln-transformed $AUC_{(0-T)}$, $AUC_{inf}$ and $C_{max}$. The 90% confidence intervals for the rates of least-squares means (LSM) were derived by exponentiation of the confidence intervals obtained for the difference between formulation of LSM resulting from the analysis on the ln-transformed parameters $AUC_{(0-T)}$, $AUC_{inf}$ and $C_{max}$.

Pharmacokinetic and statistical analyses were performed on the data obtained from the subjects. This data, in part, is contained in the following tables. The pharmacokinetic parameters are defined as follows:

$AUC_{(0-T)}$: The area under the plasma concentration versus time curve, from time 0 to the last measurable concentration of the administered drug, as calculated by the linear trapezoidal method.

$AUC_{inf}$: The area under the plasma concentration versus time curve from time 0 to infinity. AUC was calculated as the sum of the $AUC_{(0-T)}$ plus the ratio of the last measurable plasma concentration of the administered drug to the elimination rate constant.

$C_{max}$: The maximum measured plasma concentration of the administered drug.

CV: coefficient of variation.

TABLE 2

$AUC_{(0-T)}$ Ratio Analysis

| | $AUC_{(0-T)}$ | | | | | |
|---|---|---|---|---|---|---|
| | 100 mg dose | | | 400 mg dose (2 × 200 mg) | | |
| Subject | Formulation A (ng * h/mL) | Prometrium ® (ng * h/mL) | Formulation A/ Prometrium ® (%) | Formulation B (ng * h/mL) | Prometrium ® (ng * h/mL) | Formulation B/ Prometrium ® (%) |
| 1 | 20.74 | 15.80 | 131.3 | 74.02 | 132.04 | 56.1 |
| 2 | 5.11 | 3.25 | 157.2 | 11.58 | 21.91 | 52.9 |
| 3 | 4.79 | 5.44 | 88.0 | 15.09 | 21.50 | 70.2 |
| 4 | 13.65 | 16.78 | 81.4 | 27.99 | 55.24 | 50.7 |
| 5 | 3.27 | 5.01 | 65.2 | 15.16 | 31.00 | 48.9 |
| 6 | 5.78 | 4.60 | 125.7 | 16.82 | 42.63 | 39.4 |
| 7 | 5.33 | 13.27 | 40.1 | 55.68 | 579.60 | 9.6 |
| 8 | 4.06 | 2.84 | 143.2 | 13.05 | 45.72 | 28.5 |
| 9 | 15.01 | 14.06 | 106.7 | 29.92 | 141.23 | 21.2 |
| 10 | 3.06 | 1.89 | 162.0 | 6.79 | 9.36 | 72.5 |
| 11 | 2.57 | 4.74 | 54.1 | 7.10 | 16.81 | 42.3 |
| 12 | 5.60 | 11.73 | 47.7 | 45.02 | 561.74 | 8.0 |
| 13 | 23.10 | 43.15 | 53.5 | 107.53 | 116.58 | 92.2 |
| 14 | 4.73 | 4.81 | 98.3 | 44.27 | 69.78 | 63.4 |
| 15 | 51.48 | 64.37 | 80.0 | 112.06 | 110.32 | 101.6 |
| 16 | 17.24 | 20.43 | 84.4 | 56.02 | 73.26 | 76.5 |
| 17 | 42.32 | 35.80 | 118.2 | 82.78 | 251.85 | 32.9 |
| 18 | 74.87 | 118.20 | 63.3 | 78.28 | 134.65 | 58.1 |
| 19 | 2.39 | 2.79 | 85.4 | 13.76 | 37.06 | 37.1 |

TABLE 2-continued

AUC$_{(0-T)}$ Ratio Analysis

| | AUC$_{(0-T)}$ | | | | | |
|---|---|---|---|---|---|---|
| | 100 mg dose | | | 400 mg dose (2 × 200 mg) | | |
| Subject | Formulation A (ng * h/mL) | Prometrium ® (ng * h/mL) | Formulation A/ Prometrium ® (%) | Formulation B (ng * h/mL) | Prometrium ® (ng * h/mL) | Formulation B/ Prometrium ® (%) |
|---|---|---|---|---|---|---|
| 21 | 8.46 | 21.03 | 40.2 | 19.93 | 66.19 | 30.1 |
| 22 | 4.24 | 4.14 | 102.5 | 32.89 | 42.15 | 78.0 |
| 23 | 2.36 | 3.49 | 67.7 | — | 31.07 | — |
| 24 | 1.72 | 4.47 | 38.4 | 6.94 | 7.41 | 93.6 |
| 25 | 3.81 | 6.25 | 60.9 | 10.23 | 17.18 | 59.5 |
| 26 | 5.90 | 8.14 | 72.5 | 17.12 | 14.49 | 118.1 |
| 27 | 7.23 | 4.03 | 179.4 | 30.65 | 42.46 | 72.2 |
| 28 | 2.95 | 5.08 | 58.0 | 14.24 | 25.57 | 55.7 |
| 29 | 1.95 | 1.94 | 100.2 | 6.03 | 5.84 | 103.2 |
| 30 | 2.49 | 2.42 | 103.1 | 8.83 | 13.37 | 66.0 |
| Mean | 11.938 | 15.517 | 89.95 | 34.278 | 93.725 | 58.52 |
| ± SD | 16.9229 | 24.3027 | 38.421 | 31.0888 | 143.0079 | 27.931 |
| CV % | 141.8 | 156.6 | 42.7 | 90.7 | 152.6 | 47.7 |
| Minimum | 1.72 | 1.89 | 38.4 | 6.03 | 5.84 | 8.0 |
| Maximum | 74.87 | 118.20 | 179.4 | 112.06 | 579.60 | 118.1 |
| n | 29 | 29 | 29 | 28 | 29 | 28 |

TABLE 3

C$_{max}$ Ratio Analysis

| | C$_{max}$ | | | | | |
|---|---|---|---|---|---|---|
| | 100 mg dose | | | 400 mg dose (2 × 200 mg) | | |
| Subject | Formulation A (ng/mL) | Prometrium ® (ng/mL) | Formulation A/ Prometrium ® (%) | Formulation B (ng/mL) | Prometrium ® (ng/mL) | Formulation B/ Prometrium ® (%) |
|---|---|---|---|---|---|---|
| 1 | 5.840 | 7.510 | 77.8 | 12.100 | 27.900 | 43.4 |
| 2 | 1.670 | 0.793 | 210.6 | 3.180 | 8.450 | 37.6 |
| 3 | 1.330 | 2.020 | 65.8 | 3.170 | 5.360 | 59.1 |
| 4 | 4.800 | 4.590 | 104.6 | 3.480 | 8.970 | 38.8 |
| 5 | 0.982 | 1.400 | 70.1 | 2.340 | 9.230 | 25.4 |
| 6 | 1.260 | 1.470 | 85.7 | 3.900 | 13.500 | 28.9 |
| 7 | 1.600 | 9.660 | 16.6 | 9.730 | 272.000 | 3.6 |
| 8 | 1.530 | 1.180 | 129.7 | 4.060 | 24.700 | 16.4 |
| 9 | 1.410 | 4.180 | 33.7 | 5.640 | 96.000 | 5.9 |
| 10 | 1.120 | 0.499 | 224.4 | 1.540 | 2.290 | 67.2 |
| 11 | 0.560 | 1.660 | 33.7 | 1.330 | 3.790 | 35.1 |
| 12 | 2.570 | 7.370 | 34.9 | 16.200 | 243.000 | 6.7 |
| 13 | 5.320 | 20.900 | 25.5 | 21.700 | 40.600 | 53.4 |
| 14 | 0.795 | 1.290 | 61.6 | 14.000 | 19.000 | 73.7 |
| 15 | 16.500 | 46.800 | 35.3 | 39.800 | 35.300 | 112.7 |
| 16 | 4.140 | 4.380 | 94.5 | 10.300 | 17.000 | 60.6 |
| 17 | 13.700 | 13.800 | 99.3 | 23.400 | 104.000 | 22.5 |
| 18 | 29.100 | 35.900 | 81.1 | 22.000 | 28.500 | 77.2 |
| 19 | 0.607 | 0.632 | 96.0 | 2.720 | 19.400 | 14.0 |
| 21 | 2.290 | 7.310 | 31.3 | 3.220 | 14.600 | 22.1 |
| 22 | 1.280 | 1.490 | 85.9 | 7.410 | 9.830 | 75.4 |
| 23 | 0.833 | 1.280 | 65.1 | — | 13.800 | — |
| 24 | 0.589 | 0.528 | 111.6 | 1.190 | 2.040 | 58.3 |
| 25 | 0.768 | 1.540 | 49.9 | 1.480 | 3.450 | 42.9 |
| 26 | 2.280 | 4.090 | 55.7 | 4.920 | 4.970 | 99.0 |
| 27 | 0.901 | 0.682 | 132.1 | 15.900 | 15.100 | 105.3 |
| 28 | 0.747 | 1.170 | 63.8 | 2.680 | 3.760 | 71.3 |
| 29 | 0.711 | 0.687 | 103.5 | 1.540 | 1.650 | 93.3 |
| 30 | 0.618 | 0.465 | 132.9 | 1.570 | 2.780 | 56.5 |
| Mean | 3.6500 | 6.3888 | 83.20 | 8.5893 | 36.2403 | 50.23 |
| ± SD | 6.15896 | 10.82135 | 49.632 | 9.22374 | 66.10605 | 30.955 |
| CV % | 168.7 | 169.4 | 59.7 | 107.4 | 182.4 | 61.6 |
| Minimum | 0.560 | 0.465 | 16.6 | 1.190 | 1.650 | 3.6 |
| Maximum | 29.100 | 46.800 | 224.4 | 39.800 | 272.000 | 112.7 |
| n | 29 | 29 | 29 | 28 | 29 | 28 |

TABLE 4

Plasma Progesterone Concentrations (ng/mL) at 0-4 Hours
Following Treatment with Formulation B (200 mg)

| Subject ID | Period | Sampling Time (h) | | | | | | | | |
|---|---|---|---|---|---|---|---|---|---|---|
| | | 0 | 0.5 | 1 | 1.5 | 2 | 2.5 | 3 | 3.5 | 4 |
| 1 | 4 | BLQ | 0.713 | 1.250 | 2.000 | 7.890 | 6.710 | 8.610 | 7.200 | 5.210 |
| 2 | 2 | BLQ | 0.103 | 0.231 | 0.378 | 0.814 | 1.020 | 1.080 | 1.170 | 0.962 |
| 3 | 3 | BLQ | 0.619 | 3.210 | 2.590 | 2.050 | 1.860 | 1.560 | 1.390 | 1.500 |
| 4 | 3 | BLQ | 0.186 | 2.170 | 1.580 | 1.190 | 1.060 | 0.875 | 0.932 | 0.862 |
| 5 | 1 | BLQ | BLQ | 0.300 | 0.524 | 1.310 | 1.260 | 0.996 | 0.861 | 0.980 |
| 6 | 5 | BLQ | 0.626 | 2.340 | 1.900 | 1.470 | 1.890 | 1.500 | 1.230 | 1.710 |
| 7 | 2 | BLQ | 0.114 | 3.320 | 6.850 | 3.330 | 2.310 | 1.540 | 2.490 | 2.210 |
| 8 | 2 | BLQ | 0.362 | 2.000 | 1.320 | 1.060 | 0.831 | 0.947 | 0.873 | 0.607 |
| 9 | 2 | BLQ | 0.396 | 3.390 | 4.730 | 3.720 | 3.420 | 2.810 | 2.820 | 2.470 |
| 10 | 4 | BLQ | 0.381 | 2.470 | 2.620 | 2.080 | 1.710 | 1.050 | 0.670 | 0.504 |
| 11 | 3 | BLQ | BLQ | 0.390 | 0.380 | 0.354 | 0.593 | 0.447 | 0.395 | 0.301 |
| 12 | 4 | BLQ | 0.679 | 5.100 | 6.720 | 3.440 | 3.140 | 2.580 | 1.610 | 1.500 |
| 13 | 5 | BLQ | 0.682 | 9.150 | 12.900 | 12.300 | 12.300 | 10.500 | 7.900 | 6.920 |
| 14 | 1 | BLQ | 0.451 | 1.160 | 1.000 | 1.230 | 1.380 | 1.210 | 1.020 | 1.020 |
| 15 | 2 | BLQ | 0.104 | 1.010 | 4.230 | 25.700 | 32.500 | 30.000 | 21.600 | 42.800 |
| 16 | 3 | BLQ | 0.423 | 2.190 | 2.720 | 2.970 | 3.410 | 2.830 | 3.640 | 2.910 |
| 17 | 3 | BLQ | 4.160 | 5.000 | 4.320 | 14.600 | 16.800 | 11.600 | 9.740 | 8.160 |
| 18 | 1 | BLQ | 0.133 | 0.505 | 3.220 | 17.500 | 29.100 | 21.800 | 21.500 | 33.800 |
| 19 | 4 | BLQ | 0.231 | 1.280 | 1.480 | 1.100 | 1.010 | 0.761 | 0.597 | 0.574 |
| 21 | 3 | BLQ | 0.317 | 1.400 | 3.390 | 4.090 | 5.680 | 7.270 | 6.000 | 5.080 |
| 22 | 1 | BLQ | BLQ | 0.503 | 2.280 | 1.900 | 1.890 | 1.820 | 1.760 | 1.380 |
| 24 | 5 | BLQ | BLQ | 0.122/T | 0.141 | 0.169 | 0.608 | 0.468 | 0.424 | 0.485 |
| 25 | 5 | BLQ | BLQ | 0.281 | 0.749 | 1.140 | 1.320 | 1.980 | 1.360 | 1.170 |
| 26 | 1 | BLQ | BLQ | BLQ | 0.250 | 2.360 | 1.520 | 1.460 | 1.350 | 1.590 |
| 27 | 4 | BLQ | 0.166 | 0.615 | 0.770 | 0.733 | 0.741 | 0.542 | 0.436 | 0.422 |
| 28 | 5 | BLQ | 0.236 | 2.250 | 1.190 | 0.927 | 0.836 | 0.558 | 1.020 | 1.320 |
| 29 | 4 | BLQ | BLQ | 0.275 | 0.387 | 0.801 | 0.854 | 0.610 | 0.580 | 0.514 |
| 30 | 5 | BLQ | BLQ | 0.202 | 0.294 | 0.490 | 0.669 | 0.726 | 0.690 | 0.450 |
| Mean | | 0.0000 | 0.3958 | 1.8612 | 2.5326 | 4.1685 | 4.8722 | 4.2189 | 3.6164 | 4.5504 |
| ±SD | | 0.00000 | 0.77623 | 2.01493 | 2.75105 | 6.08719 | 8.20075 | 6.92960 | 5.63033 | 9.81674 |
| CV % | | 0.0 | 196.1 | 108.3 | 108.6 | 146.0 | 168.3 | 164.3 | 155.7 | 215.7 |
| Minimum | | 0.000 | 0.000 | 0.000 | 0.141 | 0.169 | 0.593 | 0.447 | 0.395 | 0.301 |
| Maximum | | 0.000 | 4.160 | 9.150 | 12.900 | 25.700 | 32.500 | 30.000 | 21.600 | 42.800 |
| n | | 28 | 28 | 28 | 28 | 28 | 28 | 28 | 28 | 28 |

M: BLQ value is set to missing
T: Time adjusted based on late blood draw
BLQ: Below Limit of Quantization
Unless otherwise specified, BLQ values sere set to zero for statistics.

TABLE 5

Plasma Progesterone Concentrations (ng/mL) at 5-24 Hours
Following Treatment with Formulation B (200 mg)

| Subject ID | Period | Sampling Time (h) | | | | | | | |
|---|---|---|---|---|---|---|---|---|---|
| | | 5 | 6 | 8 | 10 | 12 | 15 | 18 | 24 |
| 1 | 4 | 4.870 | 2.900 | 2.910 | 2.370 | 0.833 | 0.528 | 0.326 | 0.173 |
| 2 | 2 | 0.367 | 0.204 | 0.134 | 0.114 | M | M | M | 0.115 |
| 3 | 3 | 0.866 | 0.388 | 0.205 | 0.106 | 0.124 | BLQ | BLQ | BLQ |
| 4 | 3 | 0.699 | 0.332 | 0.193 | 0.441 | 0.148 | BLQ | BLQ | BLQ |
| 5 | 1 | 1.770 | 1.050 | 0.601 | 0.303 | 0.169 | 0.119 | 0.122 | BLQ |
| 6 | 5 | 0.979 | 0.369 | 0.205 | 0.158 | 0.113 | BLQ | BLQ | BLQ |
| 7 | 2 | 2.210 | 1.860 | 1.930 | 0.852 | 0.369 | 0.290 | 0.192 | 0.161 |
| 8 | 2 | 0.489 | 0.232 | 0.159 | 0.121 | 0.105 | BLQ | BLQ | BLQ |
| 9 | 2 | 2.260/T | 1.340 | 0.649 | 0.463 | 0.232 | 0.154 | 0.199 | 0.135 |
| 10 | 4 | 2.430 | 0.703 | 0.508 | 0.210 | 0.115 | 0.107 | BLQ | BLQ |
| 11 | 3 | 0.644 | 0.467 | 0.180/T | 0.113 | BLQ | BLQ | BLQ | BLQ |
| 12 | 4 | 1.530 | 0.703 | 0.365 | 0.353 | 0.190 | 0.177 | 0.166 | 0.108 |
| 13 | 5 | 3.190 | 1.710 | 0.772 | 0.510 | 0.401 | 0.359 | 0.271 | 0.188 |
| 14 | 1 | 1.290 | 0.859 | 0.288 | 0.171 | 0.141 | 0.473 | BLQ | BLQ |
| 15 | 2 | 15.400 | 5.600 | 3.350 | 1.890 | 1.640 | 1.030 | 0.758 | 0.500 |
| 16 | 3 | 2.080 | 1.530 | 0.793/T | 0.401 | 0.236 | 0.230 | 0.269 | BLQ |
| 17 | 3 | 3.590 | 2.290 | 1.300/T | 0.858 | 0.583 | 0.443 | 0.429 | 0.307 |
| 18 | 1 | 11.300 | 4.720 | 2.210 | 1.370 | 1.140 | 0.876 | 0.710 | 0.465 |
| 19 | 4 | 0.842/T | 0.565 | 0.508 | 0.375 | 0.145 | 0.109 | M | 0.105 |
| 21 | 3 | 5.160 | 2.530 | 0.865/T | 0.680 | 0.401 | 0.305 | 0.257 | 0.222 |
| 22 | 1 | 1.850 | 0.813 | 0.318 | 0.158 | 0.150 | 0.127 | BLQ | BLQ |
| 24 | 5 | 0.761 | 0.276 | 0.121 | 0.117 | BLQ | BLQ | BLQ | BLQ |

TABLE 5-continued

Plasma Progesterone Concentrations (ng/mL) at 5-24 Hours
Following Treatment with Formulation B (200 mg)

| Subject ID | Period | Sampling Time (h) | | | | | | | |
|---|---|---|---|---|---|---|---|---|---|
| | | 5 | 6 | 8 | 10 | 12 | 15 | 18 | 24 |
| 25 | 5 | 0.604 | 0.326 | 0.173 | 0.106 | BLQ | BLQ | BLQ | BLQ |
| 26 | 1 | 0.762 | 0.504 | 0.256 | 0.131 | BLQ | BLQ | BLQ | BLQ |
| 27 | 4 | 0.540 | 0.378 | 0.184 | 0.175 | 0.104 | 0.111 | 0.110 | BLQ |
| 28 | 5 | 0.704 | 0.372/T | 0.208/T | 0.141/T | M | M | 0.106/T | BLQ/T |
| 29 | 4 | 0.434 | 0.228 | BLQ | BLQ | BLQ | BLQ | BLQ | BLQ |
| 30 | 5 | 0.355 | 0.163 | BLQ | BLQ | BLQ | BLQ | BLQ/T | BLQ |
| Mean | | 2.4277 | 1.1933 | 0.6923 | 0.4531 | 0.2823 | 0.2092 | 0.1506 | 0.0885 |
| ±SD | | 3.39026 | 1.35618 | 0.87225 | 0.56752 | 0.38636 | 0.27346 | 0.21294 | 0.14085 |
| CV % | | 139.6 | 113.7 | 126.0 | 125.3 | 136.9 | 130.7 | 141.4 | 159.1 |
| Minimum | | 0.355 | 0.163 | 0.000 | 0.000 | 0.000 | 0.000 | 0.000 | 0.000 |
| Maximum | | 15.400 | 5.600 | 3.350 | 2.370 | 1.640 | 1.030 | 0.758 | 0.500 |
| n | | 28 | 28 | 28 | 28 | 26 | 26 | 26 | 28 |

M: BLQ value is set to missing
T: Time adjusted based on late blood draw
BLQ: Below Limit of Quantization
Unless otherwise specified, BLQ values sere set to zero for statistics.

These examples illustrate possible methods of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. An oral pharmaceutical dosage form in a powder form contained in a pharmaceutically acceptable capsule comprising:
   (a) micronized progesterone in an amount from about 40% to about 70% by weight of the capsule contents;
   (b) an edible oil selected from the group consisting of safflower oil, linseed oil, soybean oil, corn oil, sunflower oil, sesame oil, olive oil, cottonseed oil, flaxseed oil, menhaden oil, and mixtures thereof, in an amount from about 5% to about 25% by weight of the capsule contents;
   (c) a disintegrant in an amount from about 5% to about 25% by weight of the capsule contents; and
   (d) a hydrophilic excipient in an amount ranging from about 5% to about 25% by weight of the capsule contents.

2. The dosage form of claim 1, wherein the disintegrant is crospovidone.

3. The dosage form of claim 1, wherein the hydrophilic excipient is selected from the group consisting of corn starch, potato starch, pregelatinized starch, povidone, polysorbate, mannitol, microcrystalline cellulose, sodium starch glycolate, and mixtures thereof.

4. The dosage form of claim 1, further comprising an absorbant selected from the group consisting of silicon dioxide and its derivatives, micronized silicas, lactose, lactose monohydrate, methylcellulose, microcrystalline cellulose, sugars, maltodextrin, and mixtures thereof.

5. The dosage form of claim 1, further comprising an antioxidant selected from the group consisting of adipic acid, alpha lipoic acid, ascorbyl palmitate, biotin, boron, butylated hydroxyl toluene, butylated hydroxyanisole, carotenoids, calcium citrate, sodium metabisulfate, tocopherols, and mixtures thereof.

6. The dosage form of claim 1, further comprising a lubricant selected from the group consisting of magnesium stearate, colloidal silicon dioxide, silica gel, aluminum stearate, talc, stearic acid, sodium stearate, calcium stearate, sodium stearyl fumarate, and mixtures thereof.

7. The dosage form of claim 1, wherein the powder is free flowing.

8. The dosage form of claim 1, wherein the dosage form does not contain peanut oil or peanut particles.

9. The dosage form of claim 1, wherein the drug has a mean particle size of about 1 micron to about 15 microns.

10. The dosage form of claim 1, which contains 400 mg of the micronized progesterone.

11. A kit comprising the oral pharmaceutical dosage form of claim 1.

12. The kit of claim 11, further comprising printed instructions for its use.

13. The kit of claim 12, further comprising a printed matter describing the use of the composition to treat a condition requiring oral progesterone therapy, a pre-recorded media device describing the use of the composition to treat a condition requiring oral progesterone therapy, or a planner.

14. The kit of claim 13, wherein the printed matter is a book, booklet, brochure or leaflet.

15. The kit of claim 13, wherein the pre-recorded media device a DVD, a videotape cassette, a CD-ROM, an audio-cassette, or an audio compact disk.

16. The dosage form of claim 1, wherein the micronized progesterone is in an amount of about 55% by weight of the capsule contents.

17. The dosage form of claim 1, wherein the edible oil is in an amount from about 10% to about 15% by weight of the capsule contents.

18. The dosage form of claim 1, wherein the edible oil is in an amount of about 11% by weight of the capsule contents.

19. The dosage form of claim 2, wherein the disintegrant is in an amount from about 10% to about 20% by weight of the capsule contents.

20. The dosage form of claim 2, wherein the disintegrant is in an amount of about 15% by weight of the capsule contents.

21. The dosage form of claim 1, wherein the hydrophilic excipient is in an amount of about 15% by weight of the capsule contents.

* * * * *